US011957862B2

United States Patent
Francisco et al.

(10) Patent No.: US 11,957,862 B2
(45) Date of Patent: Apr. 16, 2024

(54) APPARATUS FOR PROVIDING INSTRUMENT ACCESS THROUGH A SURGICAL ACCESS DEVICE

(71) Applicant: Titan Medical Inc., Toronto (CA)

(72) Inventors: Matthew M. Francisco, Denver, CO (US); Laura E. Bucknam, Arvada, CO (US)

(73) Assignee: Titan Medical Inc., Toronto (CA)

( * ) Notice: Subject to any disclaimer, the term of this patent is extended or adjusted under 35 U.S.C. 154(b) by 993 days.

(21) Appl. No.: 16/800,710

(22) Filed: Feb. 25, 2020

(65) Prior Publication Data

US 2021/0259735 A1    Aug. 26, 2021

(51) Int. Cl.
*A61B 17/34* (2006.01)
*A61B 1/04* (2006.01)
(Continued)

(52) U.S. Cl.
CPC ............. *A61M 39/045* (2013.01); *A61B 1/04* (2013.01); *A61B 17/0218* (2013.01);
(Continued)

(58) Field of Classification Search
CPC ............ A61B 17/3421; A61B 17/3423; A61B 17/0218
See application file for complete search history.

(56) References Cited

U.S. PATENT DOCUMENTS 7,862,554 B2    1/2011  Hegeman
8,328,761 B2 *  12/2012 Widenhouse ...... A61B 17/3462
                                                      604/164.08
(Continued)

FOREIGN PATENT DOCUMENTS

CA         2749022      4/2012
WO   WO 2011/072096    6/2011

OTHER PUBLICATIONS

Definition of conduit—https://www.dictionary.com/browse/conduit?s=t (Year: 2020).
(Continued)

*Primary Examiner* — Si Ming Ku
(74) *Attorney, Agent, or Firm* — Knobbe, Martens, Olson & Bear LLP (57) ABSTRACT

An apparatus for providing instrument access through a gel pad of a surgical access device disposed to seal an opening to a body cavity of a patient is disclosed. The apparatus includes a stem having a bore extending therethrough, the stem having a length sufficient such that when the stem is inserted through the gel pad a distal end of the stem protrudes beyond an inner surface of the gel pad. The bore is sized to permit an instrument to be inserted through the bore and through the opening into the body cavity. The stem includes a flanged opening to the bore that remains external to an outer surface of the gel pad and limits the insertion of the stem through the gel pad. The apparatus also includes a displaceable seal disposed within the bore below the flanged opening, the displaceable seal being operable to seal the bore prior to insertion of the instrument and to displace to permit insertion of the instrument while maintaining the seal.

18 Claims, 5 Drawing Sheets

(51) Int. Cl.
  *A61B 17/02* (2006.01)
  *A61L 31/02* (2006.01)
  *A61M 39/04* (2006.01)
  *A61B 1/00* (2006.01)
  *A61B 1/313* (2006.01)
  *A61M 39/24* (2006.01)

(52) U.S. Cl.
  CPC ...... *A61B 17/3423* (2013.01); *A61B 17/3462* (2013.01); *A61B 17/3498* (2013.01); *A61L 31/022* (2013.01); *A61B 1/00154* (2013.01); *A61B 1/3132* (2013.01); *A61B 2017/0225* (2013.01); *A61B 2017/3464* (2013.01); *A61B 2017/3466* (2013.01); *A61M 2039/2426* (2013.01)

(56) References Cited

U.S. PATENT DOCUMENTS

| | | | |
|---|---|---|---|
| 8,545,450 | B2 | 10/2013 | Voegele |
| 8,926,504 | B2 | 1/2015 | Okoniewski |
| 2006/0224174 | A1 | 10/2006 | Smith |
| 2009/0234293 | A1* | 9/2009 | Albrecht ............ A61B 17/3421 604/167.03 |
| 2010/0228094 | A1 | 9/2010 | Ortiz |
| 2010/0312066 | A1 | 12/2010 | Cropper |
| 2011/0060193 | A1* | 3/2011 | Albrecht ................ A61B 90/40 600/208 |
| 2012/0190932 | A1 | 7/2012 | Okoniewski |
| 2013/0245381 | A1* | 9/2013 | Dang ................ A61B 17/3423 600/235 |
| 2018/0242962 | A1* | 8/2018 | Walen ............ A61B 17/320758 |

OTHER PUBLICATIONS

Applied Medical, Kii Balloon Blunt Tip System, downloaded on Dec. 27, 2018 in 2 pages.
Applied Medical, Kii Access Systems, 2017 in 8 pages.

\* cited by examiner

APPARATUS FOR PROVIDING INSTRUMENT ACCESS THROUGH A SURGICAL ACCESS DEVICE

BACKGROUND

1. Field

This disclosure relates to surgical procedures and more particularly to an apparatus for providing access to a body cavity of a patient for robotic and/or laparoscopic surgical instruments and equipment during a medical or surgical procedure.

2. Description of Related Art

In robotic and laparoscopic surgery, it is common to provide access to a body cavity of a patient through an access device, including a gel based access device. One such access device is the GelPort® laparoscopic system available from Applied Medical Resources Corporation of California, USA which is typically used in conjunction with an Alexis® wound protector/retractor. An incision is typically made in a wall of the body cavity and the wound protector inserted to hold open and protect the incision. The GelPort access device is secured to an outer ring of the wound protector to seal the incision and to provide access for instruments and/or the surgeon's hand through a relatively thick gel pad. The gel pad is self-sealing when the instrument is removed. In some cases, the instrument is not inserted directly through the gel pad, but is rather inserted through an access apparatus or trocar previously or thereafter inserted through the gel pad to provide specific access for certain instruments or tools.

SUMMARY

In accordance with one disclosed aspect, there is provided an apparatus for providing instrument access through a gel pad of a surgical access device disposed to seal an opening to a body cavity of a patient. The apparatus can include a stem having a bore extending therethrough. The stem can be of a length sufficient such that when the stem is inserted through the gel pad a distal end of the stem protrudes beyond an inner surface of the gel pad. The bore can be sized to permit an instrument to be inserted through the bore and through the opening into the body cavity. The stem can include a flanged opening to the bore that remains external to an outer surface of the gel pad and limits the insertion of the stem through the gel pad. The apparatus can include a displaceable seal disposed within the bore below the flanged opening. The displaceable seal can be configured to seal the bore prior to insertion of the instrument and to displace to permit insertion of the instrument while maintaining the seal.

At least a portion of the displaceable may extend through a portion of the bore enclosed by the gel pad when the stem is inserted through the gel pad.

The bore may be sized to facilitate pivoting of the instrument within the bore for positioning of the instrument within the body cavity. Height of the flanged opening may be reduced in proportion to the length of the stem to facilitate an increased pivoting angle of the instrument.

The height of the flanged opening may be about 4 millimeters.

The apparatus may include an annular flange disposed at an end of the stem distal to the flanged opening. The annular flange may be configured to bear against the inner surface of the gel pad when the stem may be inserted through the gel pad.

The seal may include cross-slit valve oriented to prevent insufflation gas from escaping prior to insertion of the instrument through the seal.

The seal may include an annular seal that bears against an outer surface of the instrument to prevent escape of insufflation gas after insertion of the instrument through the seal.

The instrument may be received within an insertion device. The bore may be sized to permit insertion of the insertion device through the stem.

The insertion device may be configured to receive more than one instrument.

The insertion device may be configured to receive a camera for insertion into the body cavity of the patient. The camera may be configured to capture images of the body cavity.

The flanged opening may have a diameter selected to be smaller than a diameter of the gel pad such that after insertion of the stem through the gel pad there remains an open area of the gel pad that is of sufficient size to accommodate insertion of at least one additional instrument directly through the gel pad adjacent to the flanged opening.

The gel pad may have a diameter of about 110 millimeters. The flanged opening may have a diameter of about 47 millimeters.

The stem may include a flexible guide disposed proximate the flanged opening. The stem may be configured to guide the instrument toward a center of the displaceable seal during insertion of the instrument through the bore.

The stem may include a first stem portion having a length sufficient to extend at least through the gel pad up to the opening in the body cavity. The stem may include a second stem portion coupled to extend the first stem portion by a length sufficient to cause a distal end of the stem to enter the body cavity when the stem is inserted through the gel pad of the surgical access device.

The second stem portion may include one of a plurality of second stem portions having different lengths. The second stem portion may be selected from the plurality of second stem portions based on a thickness of a wall of the body cavity of the patient.

Each of the plurality of second stem portions (for example, the lengths of the plurality of the second stem portions) may be associated with a body mass index (BMI) of the patient.

The flanged opening may include a port for connecting to a source of pressurized gas for insufflating the body cavity of the patient. The port may be connected through a conduit in the stem to an opening proximate a distal end of the stem for delivering the insufflation pressure to the body cavity.

The stem may be fabricated from a stainless steel material suitable for reuse following sterilization.

The displaceable valve may be removably inserted within the stainless steel stem to permit removal of the displaceable valve for discarding after a single use.

The apparatus may include an obturator sized to be received within the bore of the stem and having a piercing end that extends beyond the distal end of the stem. The piercing end of the obturator may be configured to pierce the gel pad to facilitate insertion of the stem through the gel pad.

The surgical access device may include a wound retractor having a flexible inner ring, an outer ring, and a cylindrical sleeve extending between the inner ring and the outer ring. The inner ring may be insertable through an incision in a wall of the patient's body cavity for retracting the incision to provide access. The surgical access device may include a gel cap including the gel pad. The gel cap may be received and secured to the outer ring of the wound retractor.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
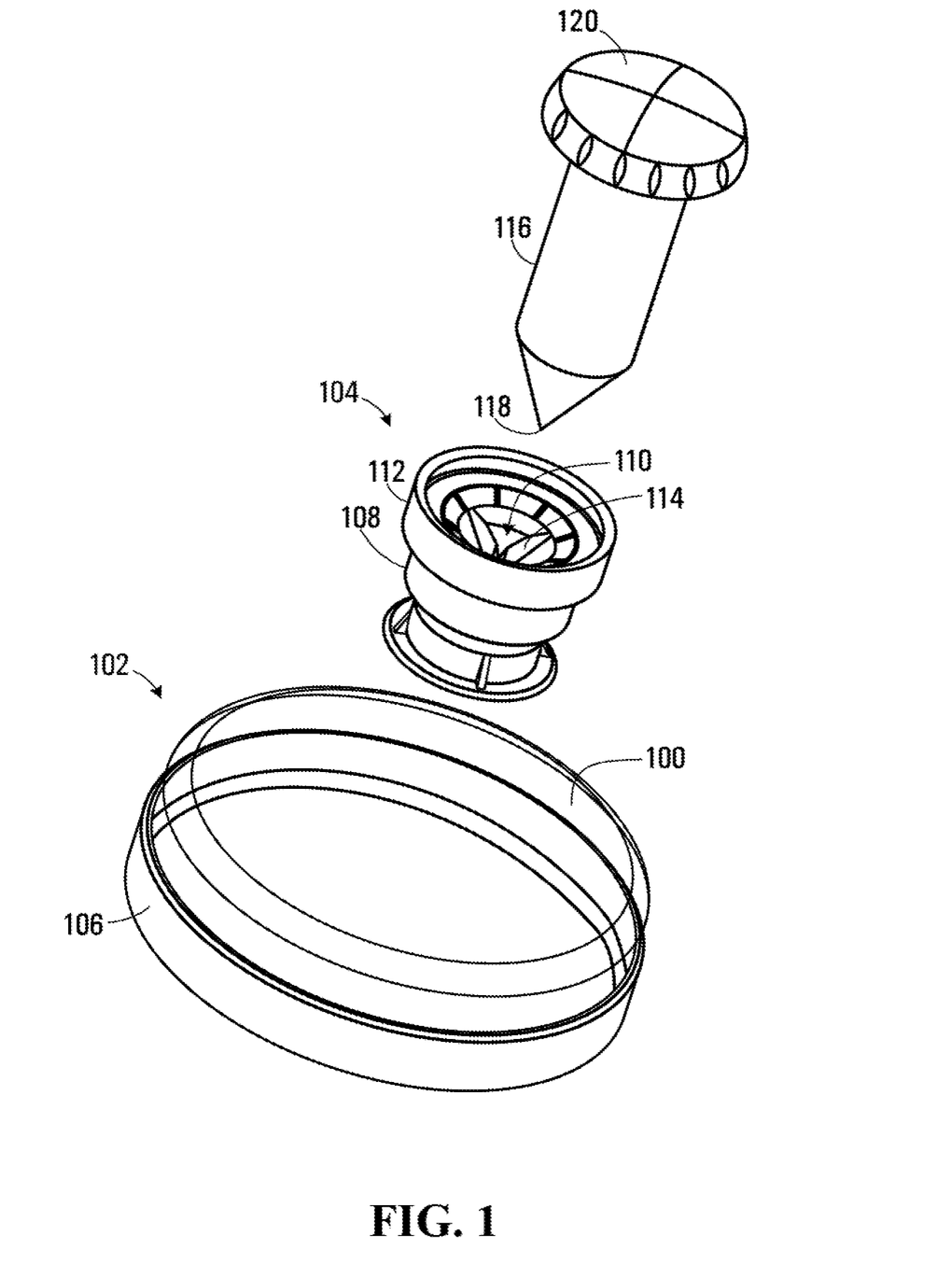
FIG. 1 is a perspective view of a surgical access device and an apparatus for providing instrument access through a gel pad of the surgical access device.
Figure 2:
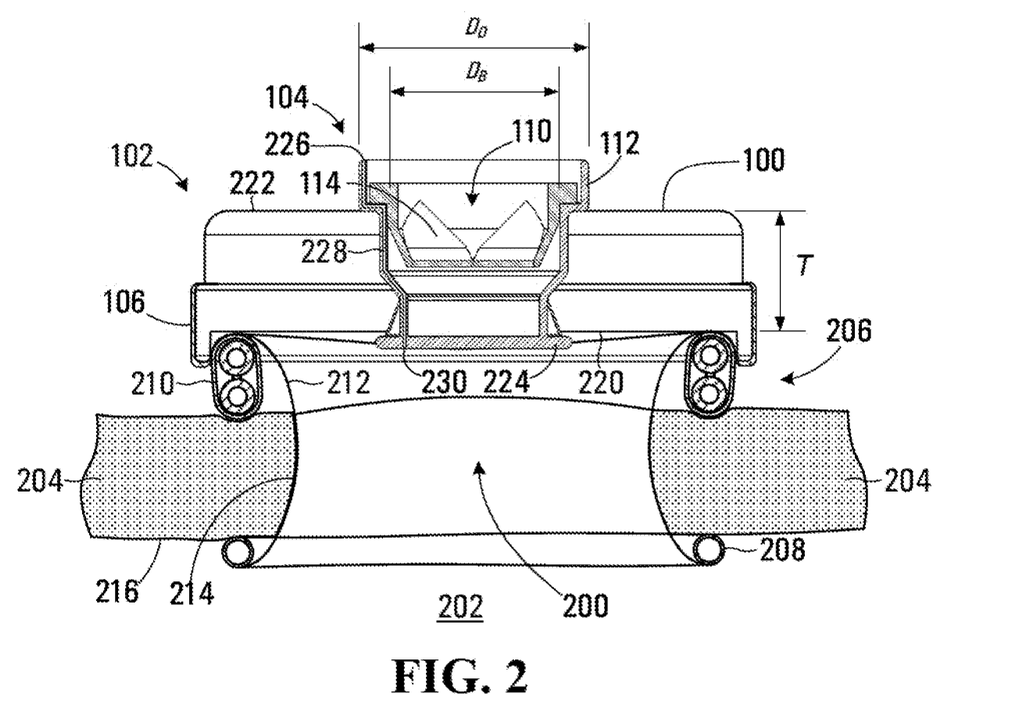
FIG. 2 is a cross sectional view of the surgical access device and the apparatus shown in FIG. 1 sealing a body cavity of a patient.

Referring to FIG. 1, an apparatus for providing instrument access through a gel pad 100 of a surgical access device 102 is shown generally at 104. The surgical access device 102 includes an annular ring 106 retaining the gel pad 100, which is formed from an elastomeric gel molded within the ring. Referring to FIG. 2, the surgical access device 102 is shown in cross section disposed to seal an opening 200 to a body cavity 202 of a patient. The opening 200 may be provided by a surgeon making an incision in a body wall 204 of the patient. As illustrated, a wound retractor 206 has been inserted to hold the incision open. The wound retractor 206 includes a flexible inner ring 208, an outer ring 210, and a cylindrical sleeve 212 extending between the outer ring and the inner ring. Once the incision is made, the inner ring 208 is resiliently deformed and inserted through the incision into the body cavity 202 while the outer ring 210 remains external to the body cavity 202. The inner ring 208 springs back into shape and bears against an inner surface 216 of the body wall 204 stretching the cylindrical sleeve 212 and causing the sleeve 212 to bear on sides 214 of the incision for holding the incision open to provide the opening 200. The annular ring 106 of the surgical access device 102 snaps over the outer ring 210 of the wound retractor 206 and the gel pad 100 seals the opening 200 thus maintaining sterile conditions.

Referring back to FIG. 1, the apparatus 104 includes a stem 108 having a bore 110 extending through the stem. The apparatus 104 also includes a flanged opening 112 to the bore 110 and a displaceable seal 114 disposed within the bore below the flanged opening. The apparatus 104 may be supplied together with an obturator 116 sized to be received within the bore 110 of the stem 108. The obturator 116 may include a piercing end 118 and a rounded or bearing end 120. In some cases, the bearing end 120 may have other shapes or configurations including having a curved surface to facilitating grasping or bearing on the end by a user. In some cases, the obturator may be omitted, and the gel pad 100 may otherwise be punctured to facilitate insertion of the apparatus 104 therethrough. As an example, a biopsy punch may be used to puncture the gel pad 100 and to remove a gel slug prior to insertion of the apparatus 104.

Figure 3:
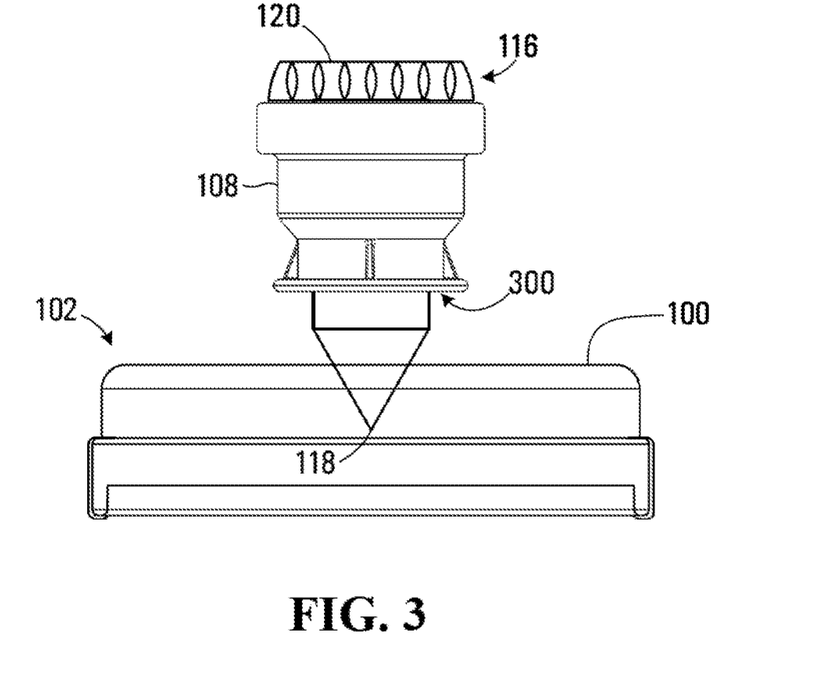
FIG. 3 is an elevational view of the apparatus shown in FIG. 1 being inserted into a gel pad of the surgical access device.

Referring to FIG. 3, for insertion of the apparatus 104 into the gel pad 100 of the surgical access device 102, the obturator 116 is inserted through the bore 110 such that the piercing end 118 protrudes below a distal end 300 of the stem 108. The piercing end 118 is then used to pierce the gel pad 100 by pressing on the bearing end 120 to force the stem 108 through the gel pad 100. The obturator 116 may then be withdrawn leaving the apparatus 104 retained within the gel pad 100. Referring back to FIG. 2, the stem 108 has a sufficient length such that when the stem is inserted through the gel pad 100, the distal end 300 of the stem protrudes beyond an inner surface 220 of the gel pad. The flanged opening 112 of the stem 108 remains external to an outer surface 222 of the gel pad and limits the insertion of the stem through the gel pad. As shown, the stem 108 also includes an annular flange 224 at the end 300 of the stem distal to the flanged opening 112. After insertion of the apparatus 104, the annular flange 224 bears against a portion of the inner surface 220 of the gel pad 100 such that the stem 108 of the apparatus 104 is held in the gel pad between the flanges 112 and 224.

The flanged opening 112 may include a port 226 for connecting to a source of pressurized gas (not shown) for insufflating the body cavity 202 of the patient. The port 226 is connected through a conduit 228 extending through along the stem 108 to an opening 230 proximate the distal end 300 of the stem. As shown, the conduit 228 is formed within a wall of the stem 108, but in some cases, it may be provided as a tube running alongside the stem 108 between the port 226 and opening 230.

Figure 4A:
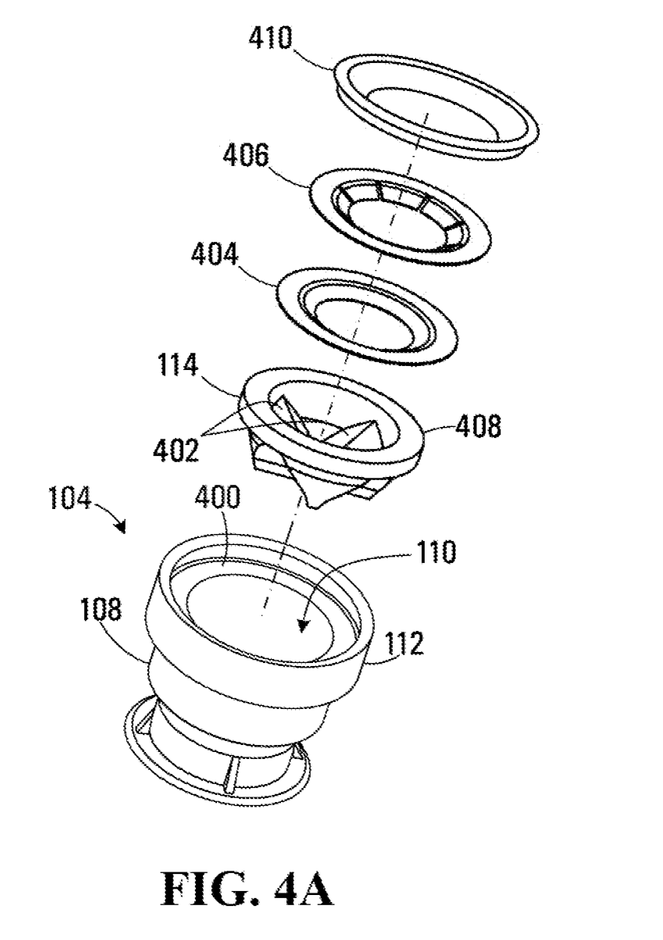
FIG. 4A is an exploded view of the apparatus shown in FIG. 1.

Referring to FIG. 4A, the displaceable seal 114 can be implemented using a cross-slit valve or double-duckbilled elastomeric seal, which is received on a seat 400 provided by the flanged opening 112. The displaceable seal 114 includes a plurality of displaceable flaps 402 and is held in place by an annular seal 404, which may be formed from a compliant material such as silicone. The apparatus 104 also includes a flexible guide 406 disposed proximate the flanged opening in the stem 108. The flexible guide 406 guides the instrument toward a center of the displaceable seal 114 during insertion of the instrument through the bore and provides a low-friction guide that prevents the instrument from catching on a lip 408 of the displaceable seal. A cap 410 may be ultrasonically welded or glued to the stem 108 to retain the flexible guide 406, annular seal 404, and displaceable seal 114 within the flanged opening 112.

Figure 4B:
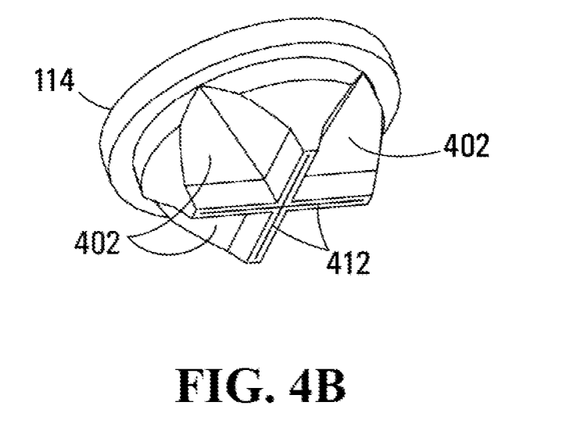
FIG. 4B is a bottom perspective view of a seal of the apparatus shown in FIG. 4A.

Referring to FIG. 4B, an underside of the displaceable seal 114 includes a pair of crossed slits 412. The body cavity 202 of the patient would generally be pressurized by an insufflation gas such as carbon dioxide and the pressure bearing on the displaceable flaps 402 keeps the pair of crossed slits 412 closed to prevent insufflation gas from escaping prior to insertion of the instrument through the displaceable seal 114. When an instrument is pushed through the displaceable seal 114, the flaps 402 are displaced to the sides thus opening the slits 412. The annular seal 404 bears against an outer surface of the instrument to maintain a seal and prevent escape of insufflation gas after insertion of an instrument.

Referring back to FIG. 2, the displaceable seal 114 can extend through a portion of the bore 110 enclosed by the gel pad 110 when the stem is inserted through the gel pad as shown in FIG. 2. The placement of the displaceable seal 114 at least partially within the bore 110 allows the flanged opening 112, which remains above the outer surface 222 of the gel pad 100, to be reduced in height.

Figure 5:
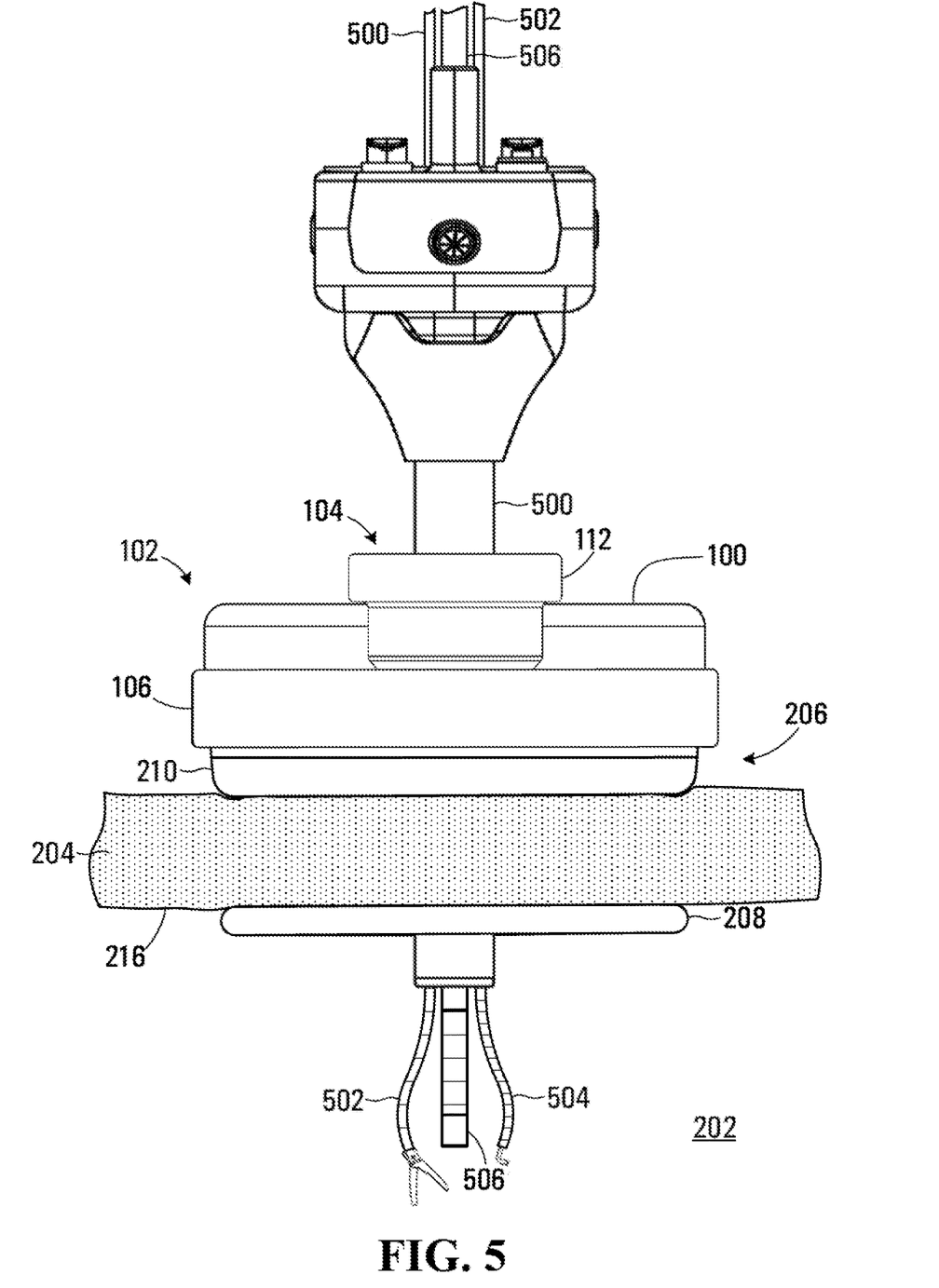
FIG. 5 is an elevational view of an insertion device being inserted through the apparatus shown in FIG. 2.

The bore of the apparatus 104 has a diameter $D_B$ sized to permit one or more instruments to be inserted through the bore into the body cavity. Referring to FIG. 5, the wound retractor 206 and surgical access device 102 are shown in elevational view within the body wall 204 of the patient. The apparatus 104 has also been inserted through the gel pad 100 of the surgical access device 102 and an insertion device 500 has been inserted. The insertion device 500 has a diameter sized to permit insertion through the bore 110 of the apparatus 104. As shown, a surgical scissor instrument 502 and a dissector hook 504 are received within the insertion device 500. The insertion device 500 includes channels receiving each of the instruments 502 and 504 and further includes a channel for receiving a camera 506 for capturing images of the body cavity 202. The insertion device 500 may include additional channels for receiving additional instruments, cameras or other accessory devices. The insertion device 500 may be implemented as described in more detail in commonly owned U.S. patent application Ser. No. 16/156,625 filed in the United States Patent and Trademark Office (USPTO) on Oct. 10, 2018 and issued as U.S. Pat. No. 10,398,287, which is incorporated herein by reference in its entirety. In some cases, an instrument may be inserted directly through the bore of the apparatus 104 into the body cavity 202.

As shown, the insertion device 500 has a diameter less than the diameter $D_B$ of the bore 110, which facilitates some pivoting of the insertion device and instruments 502, 504 within the bore. This allows some flexibility for positioning of the instruments 502 and 504 within the body cavity 202 to target a surgical site. Conventionally, an apparatus such as the apparatus 104 used with a surgical access device has a cap that remains above the outer surface 222 of the gel pad 100 and the displaceable seal, if provided, resides within the cap. As shown, the height of the flanged opening 112 is reduced in proportion to the length of the stem 108 to facilitate an increased pivoting angle of the insertion device 500 and instruments 502 and 504 within the bore 110. A height of the flanged opening 112 may be about 4 millimeters.

The flanged opening 112 also has an overall diameter Do selected to be smaller than a diameter of the gel pad 100. In some cases, there may be a need during a surgery to deploy instruments other than the instruments 500 and 502. In limiting the overall diameter of the flanged opening 112 of the apparatus 104 after insertion of the stem 108 through the gel pad 100, an open area of the gel pad remains and may be used to accommodate insertion of one or more additional instruments directly through the gel pad adjacent to the apparatus 104. As an example, a grasping tool may be used to pass a suture through for performing suturing within the body cavity 202. Alternatively, the grasping tool may be used to remove dissected tissue from the body cavity 202. As another example, a retracting tool may be used to grasp and retract tissue or otherwise hold body organs in one or more desired places during surgery. As shown, the gel pad 100 has a diameter of about 110 millimeters and the flanged opening 112 has a diameter of about 47 millimeters, leaving over 70% of the area of the gel pad 100 available for other uses.

The stem 108 and flanged opening 112 of the apparatus 104 may be fabricated from a surgical grade stainless steel material (or other surgically safe material that permits re-use upon sterilization) and the displaceable seal 114 may be removably inserted within the stainless-steel stem. The displaceable seal 114 being fabricated from an elastomeric material may only be suitable for a single use and may be discarded after use. The stem 108, flanged opening 112, and cap 410 may however be sterilized and reused.

Figure 6A:
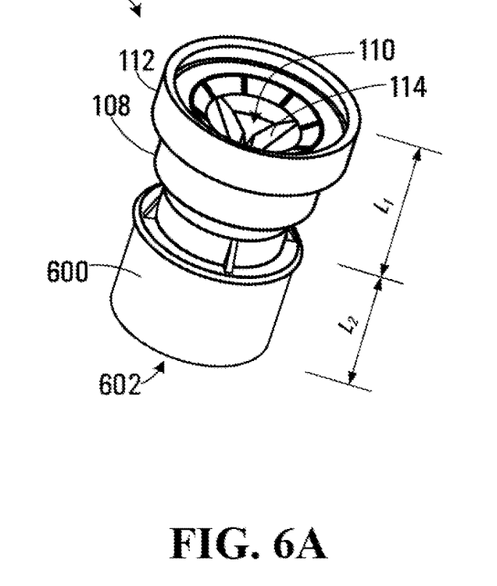
FIG. 6A is a perspective view of a modified apparatus shown in FIG. 1.

Referring to FIG. 6A, the apparatus 104 and stem 108 are shown generally configured as described above where a length $L_1$ of the stem 108 is sufficient to extend at least through a thickness of the gel pad 100. In some cases, the length $L_1$ of the stem 108 may extend below the inner surface 220 of the gel pad 100 proximate the opening in the body cavity. As shown in FIG. 6A, the apparatus 104 includes a second stem portion 600 in addition to the first stem portion 108. The second stem portion 600 has a length $L_2$ sufficient to cause a distal end 602 of the second stem portion to enter the body cavity 202 of the patient when the first and second stem portions 108 and 600 are inserted through the gel pad 100.

Figure 6B:
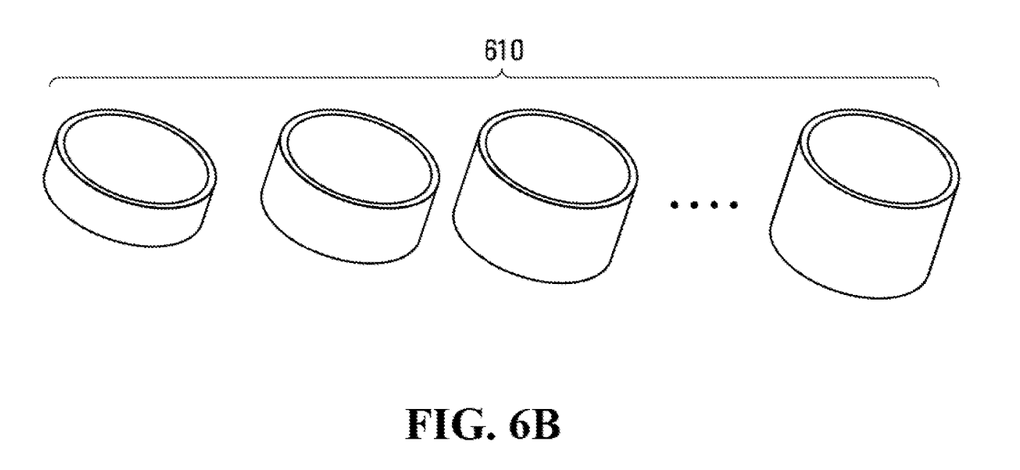
FIG. 6B is a perspective view of a set of stem portions used in conjunction with the apparatus shown in FIG. 6A.

Referring to FIG. 6B, in some cases, the apparatus 104 may be supplied together with a plurality of second stem portions shown at 610, each having a different length. One of the stem portions 610 that is appropriate for the thickness of the body wall 204 of the patient may be selected for use with the apparatus 104. The set of stem portions 610 may be fabricated from surgical stainless steel and may be reusable. In some cases, each of the stem portions 610 may be associated with a body mass index (BMI). The selection of the stem portion 610 for use on a patient undergoing surgery may thus be based on a determined BMI of the patient. The set of stem portions 610 thus provide a customized overall stem length for the apparatus 104. A selected stem portion 600 from the set of stem portions 610 may be threaded onto the stem 108 or otherwise attached, for example via a magnetic connection.

Trocars that are generally available have a limited diameter and may not be able to accommodate an insertion device that has multiple channels for accommodating instruments and/or a camera for imaging inside the body cavity. Common trocars also generally have a cap that protrudes significantly above the gel pad and limits the depth of insertion and reach of instruments within the body cavity. Trocars are also usually only available in a fixed length of trocar stem, which does not accommodate patients who have either a significant presence of or lack of adipose tissue that changes the thickness of the body wall through which the body cavity is accessed.

While specific embodiments have been described and illustrated, such embodiments should be considered illustrative only and not as limiting the disclosed embodiments as construed in accordance with the accompanying claims.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrecited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B." Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. An apparatus for providing instrument access through a gel pad of a surgical access device disposed to seal an opening to a body cavity of a patient, the apparatus comprising:

a stem including a bore extending therethrough, the stem being of a sufficient length such that when the stem is inserted through the gel pad, a distal end of the stem protrudes beyond an inner surface of the gel pad, the bore being sized to permit an instrument to be inserted through the bore and through the opening into the body cavity, the stem further including a flanged opening to the bore that remains external to an outer surface of the gel pad and limits the insertion of the stem through the gel pad;

a displaceable seal disposed within the bore below the flanged opening, the displaceable seal configured to seal the bore prior to insertion of the instrument and to displace to permit insertion of the instrument while maintaining the seal; and an annular seal comprising a complaint material and being located proximal to the displaceable seal, the annular seal bearing against an outer surface of the instrument to prevent escape of an insufflation gas after insertion of the instrument through the seal, wherein the displaceable seal comprises a cross-slit valve that includes a plurality of flaps and is positioned to prevent the insufflation gas from escaping prior to insertion of the instrument through the seal formed by the plurality of flaps of the cross-slit valve, wherein the plurality of flaps of the cross-slit valve deform to accommodate the instrument after insertion of the instrument through the displaceable seal while still preventing the insufflation gas from escaping, and wherein the stem comprises:
a first stem portion being of a length sufficient to extend at least through the gel pad up to the opening in the body cavity; and
a plurality of second stem portions with different lengths, wherein an appropriate second stem portion is coupled to extend the first stem portion by a length sufficient to cause the distal end of the stem to enter the body cavity when the stem is inserted through the gel pad of the surgical access device.

2. The apparatus of claim 1 wherein at least a portion of the displaceable seal extends through a portion of the bore enclosed by the gel pad when the stem is inserted through the gel pad.

3. The apparatus of claim 1 wherein the bore is sized to facilitate pivoting of the instrument within the bore for positioning of the instrument within the body cavity and wherein a height of the flanged opening is reduced in proportion to the length of the stem to facilitate an increased pivoting angle of the instrument.

4. The apparatus of claim 3 wherein the height of the flanged opening is about 4 millimeters.

5. The apparatus of claim 1 further comprising an annular flange disposed at an end of the stem distal to the flanged opening, the annular flange configured to bear against the inner surface of the gel pad when the stem is inserted through the gel pad.

6. The apparatus of claim 1 wherein the instrument is received within an insertion device and wherein the bore is sized to permit insertion of the insertion device through the stem.

7. The apparatus of claim 6 wherein the insertion device is configured to receive more than one instrument.

8. The apparatus of claim 6 wherein the insertion device is configured to receive a camera configured to be inserted into the body cavity of the patient, the camera configured to capture images of the body cavity.

9. The apparatus of claim 8 wherein the flanged opening has a diameter selected to be smaller than a diameter of the gel pad such that after insertion of the stem through the gel pad there remains an open area of the gel pad that is of sufficient size to accommodate insertion of at least one additional instrument directly through the gel pad adjacent to the flanged opening.

10. The apparatus of claim 9 wherein the gel pad has a diameter of about 110 millimeters and wherein the flanged opening has a diameter of about 47 millimeters.

11. The apparatus of claim 1 wherein the stem comprises a flexible guide disposed proximate the flanged opening and configured to guide the instrument toward a center of the displaceable seal during insertion of the instrument through the bore.

12. The apparatus of claim 1 wherein the appropriate second stem portion comprises one of the plurality of second stem portions with different lengths and wherein the appropriate second stem portion is selected from the plurality of second stem portions based on a thickness of a wall of the body cavity of the patient.

13. The apparatus of claim 12 wherein the lengths of the plurality of second stem portions are associated with a body mass index (BMI) of the patient.

14. The apparatus of claim 1 wherein the flanged opening comprises a port configured to connect to a source of pressurized gas for insufflating the body cavity of the patient, the port being connected through a conduit in the stem to an opening proximate a distal end of the stem for delivering an insufflation pressure to the body cavity.

15. The apparatus of claim 1 wherein the stem is fabricated from a stainless steel material suitable for reuse following sterilization.

16. The apparatus of claim 15 wherein the displaceable seal is removably inserted within the stem to permit removal of the displaceable seal for discarding after a single use.

17. The apparatus of claim 1 further comprising an obturator sized to be received within the bore of the stem and including a piercing end that extends beyond the distal end of the stem, the piercing end of the obturator configured to pierce the gel pad to facilitate insertion of the stem through the gel pad.

18. The apparatus of claim 1 wherein the surgical access device comprises:
a wound retractor including a flexible inner ring, an outer ring, and a cylindrical sleeve extending between the inner ring and the outer ring, the inner ring being insertable through an incision in a wall of the body cavity for retracting the incision to provide access; and
a gel cap including the gel pad, the gel cap being received and secured to the outer ring of the wound retractor.

* * * * *